United States Patent
Al-Qaisi

(10) Patent No.: US 10,966,607 B2
(45) Date of Patent: Apr. 6, 2021

(54) PHASE-SENSITIVE OPTICAL COHERENCE TOMOGRAPHY TO MEASURE OPTICAL ABERRATIONS IN ANTERIOR SEGMENT

(71) Applicant: Alcon Inc., Fribourg (CH)

(72) Inventor: Muhammad K. Al-Qaisi, Ladera Ranch, CA (US)

(73) Assignee: Alcon Inc., Fribourg (CH)

( * ) Notice: Subject to any disclaimer, the term of this patent is extended or adjusted under 35 U.S.C. 154(b) by 322 days.

(21) Appl. No.: 16/149,380

(22) Filed: Oct. 2, 2018

(65) Prior Publication Data

US 2019/0099077 A1  Apr. 4, 2019

Related U.S. Application Data

(60) Provisional application No. 62/566,996, filed on Oct. 2, 2017.

(51) Int. Cl.
*A61B 3/117* (2006.01)
*A61B 3/107* (2006.01)
(Continued)

(52) U.S. Cl.
CPC .............. *A61B 3/117* (2013.01); *A61B 3/102* (2013.01); *A61B 3/103* (2013.01); *A61B 3/107* (2013.01); *A61B 3/1015* (2013.01); *G01B 9/0203* (2013.01); *G01B 9/02007* (2013.01); *G01B 9/02091* (2013.01); *G01B 2290/45* (2013.01); *G01B 2290/60* (2013.01)

(58) Field of Classification Search
CPC ......... A61B 3/117; A61B 3/107; A61B 3/103; A61B 3/1015; A61B 3/102; G01B 9/02091; G01B 9/0203; G01B 9/02007; G01B 2290/45; G01B 2290/60
USPC .......................................................... 351/200
See application file for complete search history.

(56) References Cited

U.S. PATENT DOCUMENTS

| 2009/0168017 A1 | 7/2009 | O'Hara et al. |
| 2016/0166144 A1 | 6/2016 | Izatt |
| 2017/0276471 A1* | 9/2017 | Jiang .................. G01B 9/02068 |

OTHER PUBLICATIONS

Al-Qaisi, "Polarization-Sensitive Optical Coherence Tomography Using Polarization-Maintaining Fibers" [dissertation], Dec. 2010, Retrieved from the University of Minnesota Digital Conservancy, http://hdl.handle.net/11299/99238.
(Continued)

*Primary Examiner* — Mohammed A Hasan

(57) ABSTRACT

Techniques for measuring optical aberrations of the eye are disclosed. An example method comprises positioning the eye in a measurement location adjacent to a measurement arm of an optical coherence tomography (OCT) interferometer apparatus, so that source light from the measurement arm passes into the anterior segment of the eye and detecting an interference pattern, the interference pattern resulting from a combination of light reflected from the eye and light reflected from a reference arm of the OCT interferometer apparatus. Based on the interference pattern, an optical delay between a reference surface in the anterior segment of the eye and a measured surface in the eye is calculated, the reference surface being the anterior surface of the cornea or the lens, wherein said calculating comprises measuring an optical phase shift between the reference surface and the measured surface, based on the detected interference pattern.

8 Claims, 6 Drawing Sheets

(51) Int. Cl.
- *A61B 3/103* (2006.01)
- *A61B 3/10* (2006.01)
- *G01B 9/02* (2006.01)

(56) References Cited

OTHER PUBLICATIONS

Choma, et al., "Spectral-domain phase microscopy", May 15, 2005, pp. 1162-1164, vol. 30, No. 10, Optics Letters.

Fang-Yen, et al., "Noncontact measurement of nerve displacement during action potential with a dual-beam low-coherence interferometer", Sep. 1, 2004, pp. 2028-2030, vol. 29, No. 17, Optics Letters.

Joo, et al., "Spectral-domain optical coherence phase microscopy for quantitative phase-contrast imaging", Aug. 15, 2005, pp. 2131-2133, vol. 30, No. 16, Optics Letters.

Sarunic, et al., "Full-field swept-source phase microscopy", May 15, 2006, pp. 1462-1464, vol. 31, No. 10, Optics Letters.

* cited by examiner

PHASE-SENSITIVE OPTICAL COHERENCE TOMOGRAPHY TO MEASURE OPTICAL ABERRATIONS IN ANTERIOR SEGMENT

TECHNICAL FIELD

Embodiments disclosed herein are related to devices, systems, and methods for applying phase-sensitive Optical Coherence Tomography to measuring aberrations in the anterior segment of the eye.

BACKGROUND

Phase-sensitive Optical Coherence Tomography (OCT) has been developed for such applications as detecting cell membrane dynamics, where the observed motion has amplitudes less than an optical wavelength. FIG. 1 illustrates the basic components of an experimental setup for carrying out a time-domain approach to phase-sensitive OCT. As seen in the figure, a beamsplitting interferometer BS receives a composite light source, with the light supplied to the beamsplitting interferometer BS comprising the output from a continuous-wave (CW) laser, in this case with a wavelength of 775 nanometers, and a low-coherence 1550-nanometer beam from a super-luminescent diode. It should be appreciated that the wavelength of the CW laser is selected to be half that of the 1550-nanometer beam from the diode. A reference arm includes reference arm mirror M, which is movable to provide z-axis adjustments for the OCT imaging, just as is done for conventional time-domain OCT. A dichroic mirror DM splits the reflected light from reference arm mirror M and target sample 25, which combines to form a time-domain interference pattern in beamsplitting interferometer BS, to separate photodetectors D1 and D2, which are sensitive to 1550-nanometer and 775-nanometer light, respectively. The outputs from photodetectors D1 and D2 are supplied to analog-to-digital converter (ADC) circuit 20, the digital output of which is supplied to computer 30 for processing. O1 and O2 are optics in the reference and measurement arm, respectively.

The setup shown in FIG. 1 is based on a modified version of a phase-disperson optical tomography, where one of the two low-coherence optical sources used in conventional phase-dispersion optical tomography is replaced with a CW source. This approach allows for the use of a noise-cancellation method similar to that used in phase-dispersion optical tomography.

The phase-sensitivity of the technique shown in FIG. 1 is obtained by unwinding the optical phase shift between a reference interface 50 positioned between the interferometer/BS 10 and the target sample 25. This reference interface 50 is the surface of a glass coverslip 55, which is positioned against target sample 25, as seen in the figure. The physical separation between this reference interface and a measured interface in or on the target sample has a length L, and the material between them has an effective refractive index n. The rate of change of the path-length difference between the reference and the signal arms is denoted v, which includes both the translation velocity of the reference mirror and the jitter of the interferometer, and the phase of the CW heterodyne signal output received at the detector D2 can be given by:

$$\psi_{CW}(t) \approx \mathrm{mod}_{2\pi}(k_{CW} 2\int_0^t v\, dt), \qquad (1)$$

where k is the optical wave number, provided that the reference interface 50 is a strong reflector compared to the measured interface.

The situation differs for the low-coherence light. When $\int_0^t v\, dt \approx n_{LC} L$ and L is much larger than the coherence length, the low-coherence signal returned by the interferometer to detector D1 is dominated by the light reflected by the measured interface, since coherence gating suppresses light reflected by the reference interface 50. Thus, the phase of the LC heterodyne signal received at the detector D1 is given by:

$$\psi_{CW}(t) = \mathrm{mod}_{2\pi}[k_{LC} 2(\int_0^t v\, dt - n_{LC})]. \qquad (2)$$

Because the center wavelength of the low-coherence source is twice that of the CW source, such that $2k_{LC} = k_{CW}$, the difference phase, representing the phase difference between the reference interface and the measured interface, is given by:

$$\psi_D = \psi_{CW} - \psi_{LC} = \mathrm{mod}_{2\pi}(4k_{LC} n_{LC} L). \qquad (3)$$

This difference phase corresponds to the phase acquired by the low-coherence light as it traverses from the reference interface 50 to the measured interface in the target sample 25, and back to the reference interface 50, with the effects of jitter in v being eliminated. By scanning the sample and measuring this difference phase, the distance L can be measured, to sub-wavelength precision and accuracy.

FIGS. 2A and 2B illustrate the basic components of two setups for carrying out a spectral-domain approach to phase-sensitive OCT, the first setup corresponding to a Fourier-domain (FD) phase-sensitive OCT approach, where an optical source having a fixed but relatively wide optical bandwidth is used, and the second corresponding to a swept-source (SS) phase-sensitive OCT approach, where a swept optical source 70 is used. With both of these spectral-domain approaches, the CW laser source and the moving reference arm mirror used in Yang's system are not needed.

Just as in the system shown in FIG. 1, the phase-sensitive OCT systems shown in FIGS. 2A and 2B allow for the measurement of the optical phase shift as light travels from the reference interface 50 to each of one or more measured interfaces in target sample 25, and back again. Thus, these techniques depend on the presence of a high-reflectivity coverslip 55, which may be a piece of glass, for example.

Current ophthalmic refractive surgical methods, such as cataract surgery, intra-corneal inlays, laser-assisted in situ keratomileusis (LASIK), and photorefractive keratectomy (PRK), rely on ocular biometry data to prescribe the best refractive correction. Historically, ophthalmic surgical procedures used ultrasonic biometry instruments to image portions of the eye. In some cases, these biometric instruments generated a so-called A-scan of the eye: an acoustic echo signal from all interfaces along an imaging axis that was typically aligned with an optical axis of the eye: either parallel with it, or making only a small angle. Other instruments generated a so-called B-scan, essentially assembling a collection of A-scans, taken successively as a head or tip of the biometry instrument was scanned along a scanning line. This scanning line was typically lateral to the optical axis of the eye. These ultrasonic A- or B-scans were then used to measure and determine biometry data, such as an axial Length, an anterior chamber depth of the eye, or the radii of corneal curvature.

In some surgical procedures a second, separate keratometer was used to measure refractive properties and data of the cornea. The ultrasonic measurements and the refractive data were then combined in a semi-empirical formula to calculate the characteristics of the optimal intra-ocular lens (IOL) to be prescribed and inserted during the subsequent cataract surgery.

More recently, ultrasonic biometry devices have been rapidly giving way to optical imaging and biometry instruments that are built on the principle of Optical Coherence Tomography (OCT). OCT is a technique that enables micron-scale, high-resolution, cross-sectional imaging of the human retina, cornea, or cataract. OCT technology is now commonly used in clinical practice, with such OCT instruments are now used in 80-90% of all IOL prescription cases. Among other reasons, their success is due to the non-contact nature of the imaging and to the higher precision than that of the ultrasound biometers.

Even with these recent advances, however, substantial further growth and development is needed for the functionalities and performance of biometric and imaging instruments.

SUMMARY

Techniques for measuring optical aberrations of the eye are detailed below. An example method comprises positioning the eye in a measurement location adjacent to a measurement arm of an optical coherence tomography (OCT) interferometer apparatus, so that source light from the measurement arm passes into the anterior segment of the eye and detecting an interference pattern, the interference pattern resulting from a combination of light reflected from the eye and light reflected from a reference arm of the OCT interferometer apparatus. Based on the interference pattern, an optical delay between a reference surface in the anterior segment of the eye and a measured surface in the eye is calculated, the reference surface being the anterior surface of the cornea or the lens, wherein said calculating comprises measuring an optical phase shift between the reference surface and the measured surface, based on the detected interference pattern.

Time-domain-based or spectral-domain-based techniques may be used, in various embodiments. However, in contrast to the techniques described in the background section above, the reference surface in the presently disclosed techniques is a surface of the eye itself, rather than the surface of a coverslip introduced between the OCT measurement arm and the target of the measurement. Thus, the process is performed without any coverslip positioned between the eye and the measurement arm of the interferometer.

In some embodiments, the method may further comprise scanning the source light in a scan pattern across the measured surface in the eye, such that the detecting and calculating are repeated for each of a plurality of points in the scan pattern, so as to obtain an optical delay between the reference surface and the measured surface for each of the plurality of points. In some of these embodiments, the reference surface is the anterior surface of the eye's cornea and the method further comprises calculating an optical wavefront for the cornea, based on the optical delay between the reference surface and the measured surface for each of the plurality of points. In other embodiments, the reference surface is the anterior surface of the eye's lens and the method further comprises calculating an optical wavefront for the lens, based on the optical delay between the reference surface and the measured surface for each of the plurality of points.

DETAILED DESCRIPTION

In the following description, specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art may realize other material that, although not specifically described herein, is within the scope and spirit of this disclosure.

Several techniques for measuring the eye's aberrations have been described and used to characterize the eye, e.g., in connection with performing ophthalmic procedures and/or correcting for aberrations with glasses, contact lenses, or refractive surgery. Corneal laser treatments, for example, use a wavefront map of the eye, as developed from aberrometric measurements, to guide the laser during treatment. Known techniques for measuring the eye's aberrations include ray-tracing techniques and the use of a Shack-Hartmann wavefront sensor.

Conventional OCT techniques, which are based on intensity (amplitude) imaging, can provide topographic images of all the optical surfaces of the eye. However, due to tissue inhomgenity, it is doubtful that the topographic image data obtaining from conventional OCT imaging can be accurately converted to actual optical aberrations.

Figure 3:
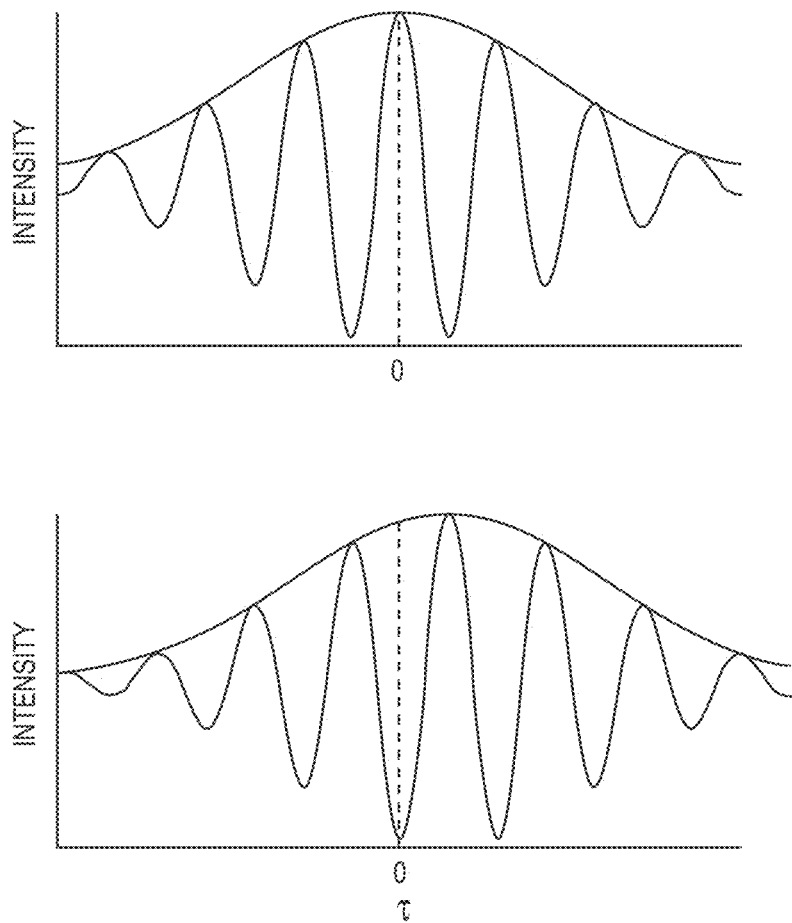
FIG. 3 illustrates differences between OCT intensity data and OCT phase-sensitive data.

An OCT phase signal, using techniques like those described in the background section above, can be used to provide measurement sensitivities down to about 20 picometers, which is several orders of magnitude better than can be achieved with conventional intensity OCT images. FIG. 3 illustrates the difference between OCT intensity and phase measurements. The top plot illustrates OCT intensity and phase information obtained from OCT signals returned from a sample before it is altered, while the bottom plot illustrates OCT intensity and phase information obtained from OCT signals returned from a sample after it is altered, i.e., after the measured surface moves a small distance. As can be seen in these plots, a small change in the sample results in a dramatic difference in phase. However, the change in the amplitude information is very small, making the change in the sample very difficult to measure with intensity information alone.

Figure 4:
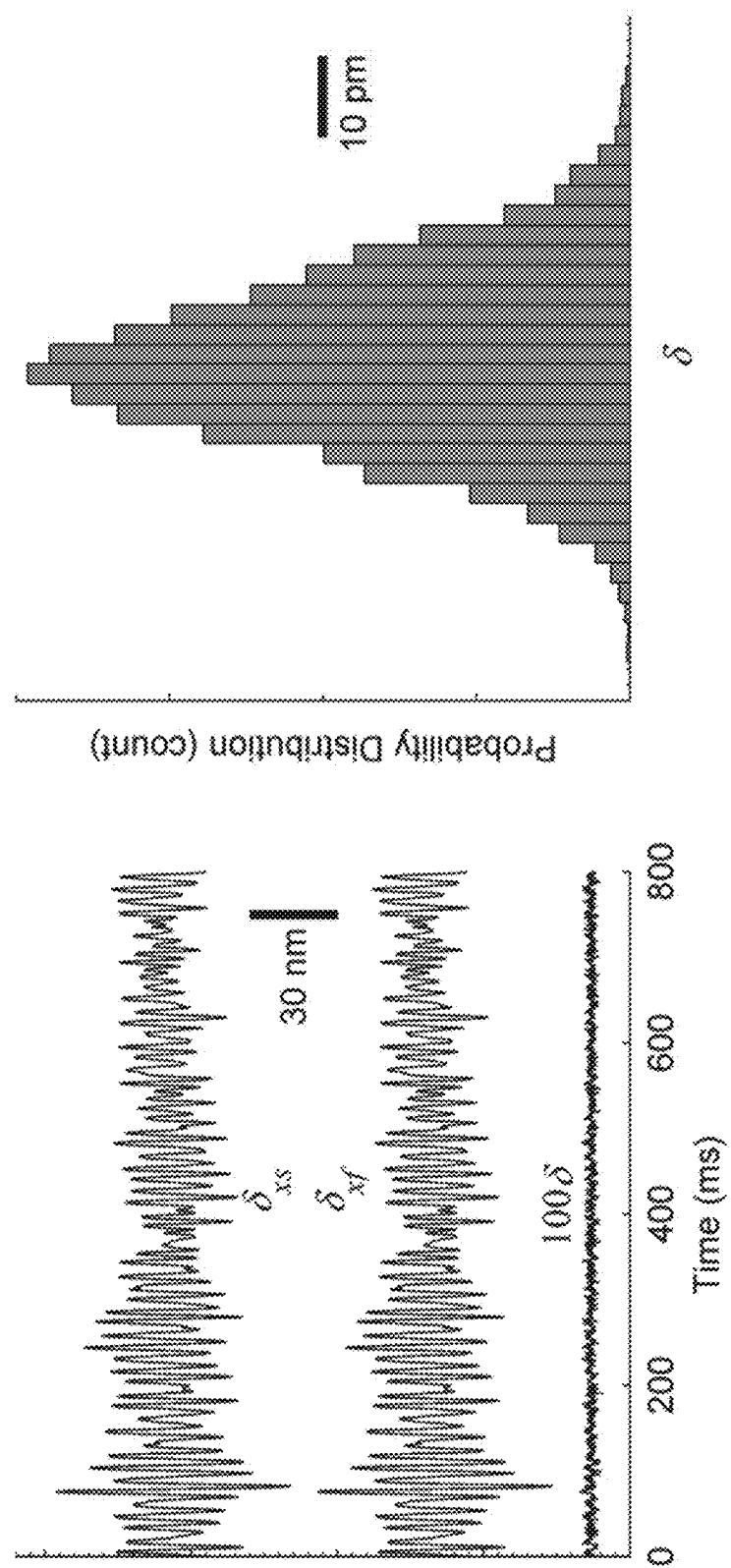
FIG. 4 shows the sensitivity of example phase-sensitive OCT measurements.

FIG. 4 illustrates quantitative results from a measurement performed by a phase-sensitive OCT system. On the left side of FIG. 4, three signals are displayed. The two signals with large variations illustrate the signal plus noise for to independent channels. It will be noted, however, that these signals have a common noise component. The third signal is the differential signal, where the common signal is removed. This represents the noise and jitter cancellation that is achieved by measuring a phase differential between a reference surface and measured surface in line with the measurement arm of the OCT interferometer, by using techniques like those described in the background section above. As shown on the right-hand side of FIG. 4, measurement sensitivities of about 20 picometers are possible According to embodiments of the present invention, phase-sensitive OCT techniques, whether based on time-domain or spectral-domain OCT processing, are applied to ophthalmic procedures, and in particular to measuring aberrations in the anterior segment of the eye and obtaining real wavefront aberration data from an OCT signal. These procedures, as described in more detail below, can be carried out without the use of a coverslip, in contrast to the techniques described in the background section above. This is accomplished by using the surfaces of the cornea and/or lens as reference planes, rather than the surface of a coverslip or other artificial reference surface positioned between the measurement arm of the OCT equipment and the measured eye.

Figure 5:
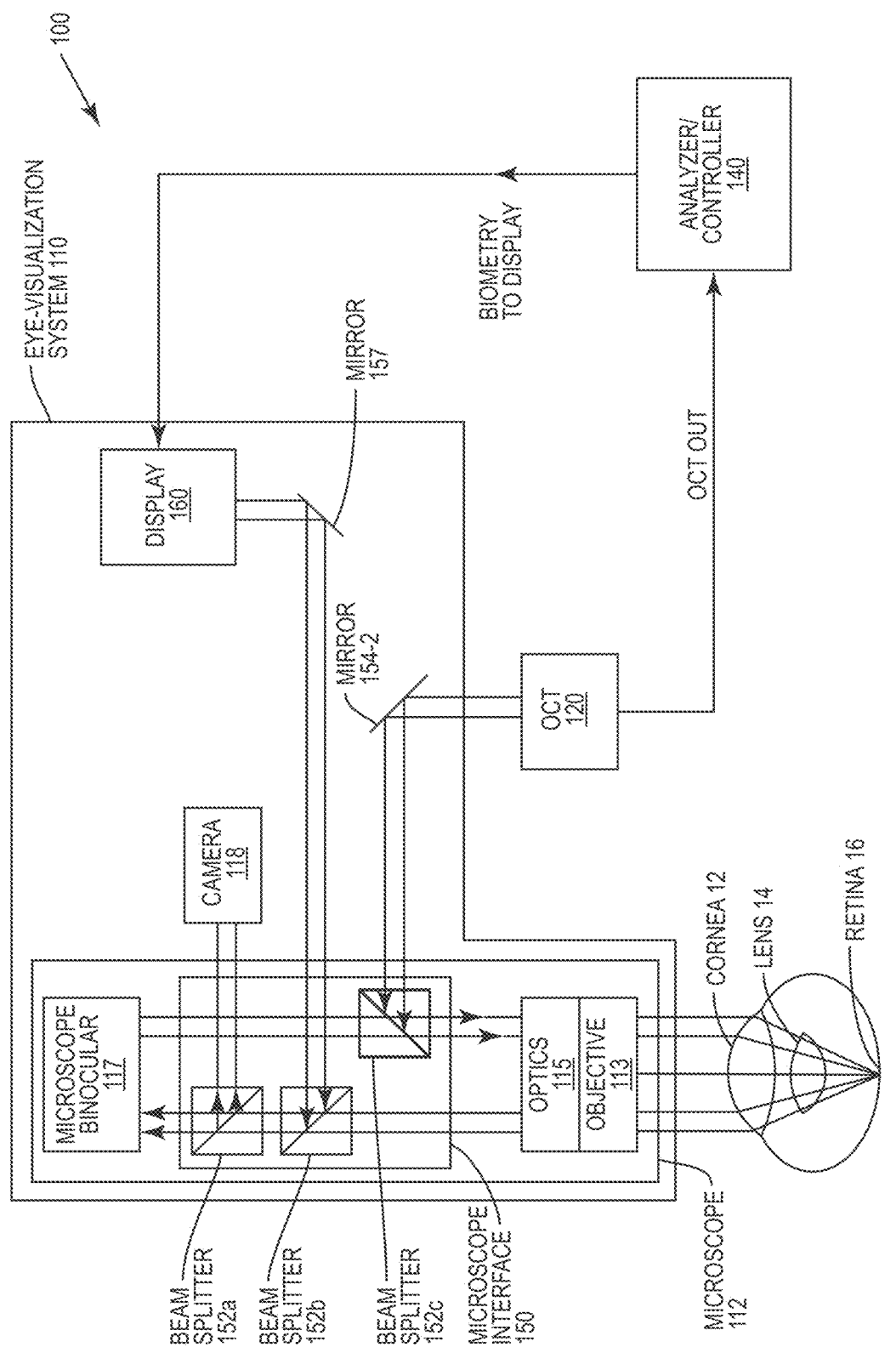
FIG. 5 is a block diagram illustrating an example phase-sensitive OCT apparatus configured to carry out one or more of the techniques described herein.

Embodiments of the presently disclosed techniques and apparatus may be employed in both microscope-mounted and microscope-integrated Optical Coherence Tomography (OCT) systems. FIG. 5 illustrates an example of a microscope-integrated OCT system 100, and is presented to illustrate the basic principles of a phase-sensitive OCT process, consistent with embodiments of the present invention.

System 100 includes an eye-visualization system 110, configured to provide a visual image of an imaged region in an eye 10, an Optical Coherence Tomographic (OCT) imaging system 120, configured to generate an OCT image of the imaged region; and an analyzer 140, configured to determine refractive characteristics of the eye based on the OCT image and based on phase-sensitive OCT measurements as described herein. It will be appreciated that the OCT imaging system 120 and the analyzer/controller 140 can be integrated into the eye visualization system 110.

System 100 may be used to image and measure aberrations of the anterior region of the eye 10, such as a target of a surgical procedure. For a corneal procedure, the measured region can be a portion of a cornea 12. For other procedures, the measured region can be a capsule and the (crystalline) lens 14 of the eye. The measured region may also include the anterior chamber of the eye.

The eye-visualization system 110 can include a microscope 112. In some embodiments, it can include a slit-lamp. The microscope 112 can be an optical microscope, a surgical microscope, a video-microscope, or a combination thereof. In the embodiment of FIG. 5, the eye-visualization system 110 (shown in thick solid line) includes the surgical microscope 112, which in turn includes an objective 113, optics 115, and a binocular or ocular 117. The eye-visualization system 110 can also include a camera 118 of a video microscope, which in the example system of FIG. 5 is coupled into the optical path of microscope binocular 117 with a beam splitter 152a.

Figure 1:
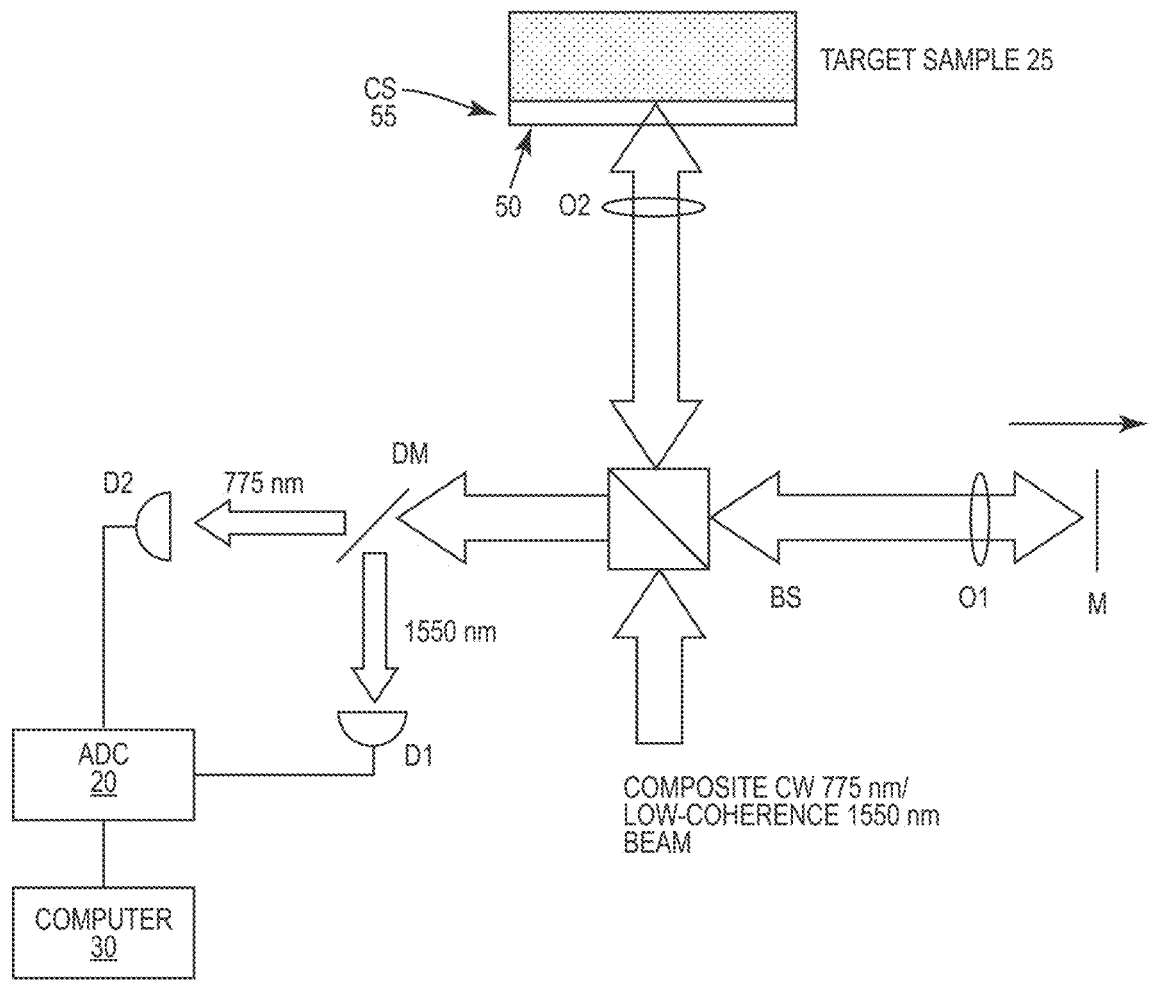
FIG. 1 is a diagram illustrating time-domain-based phase-sensitive OCT.
Figure 2A:
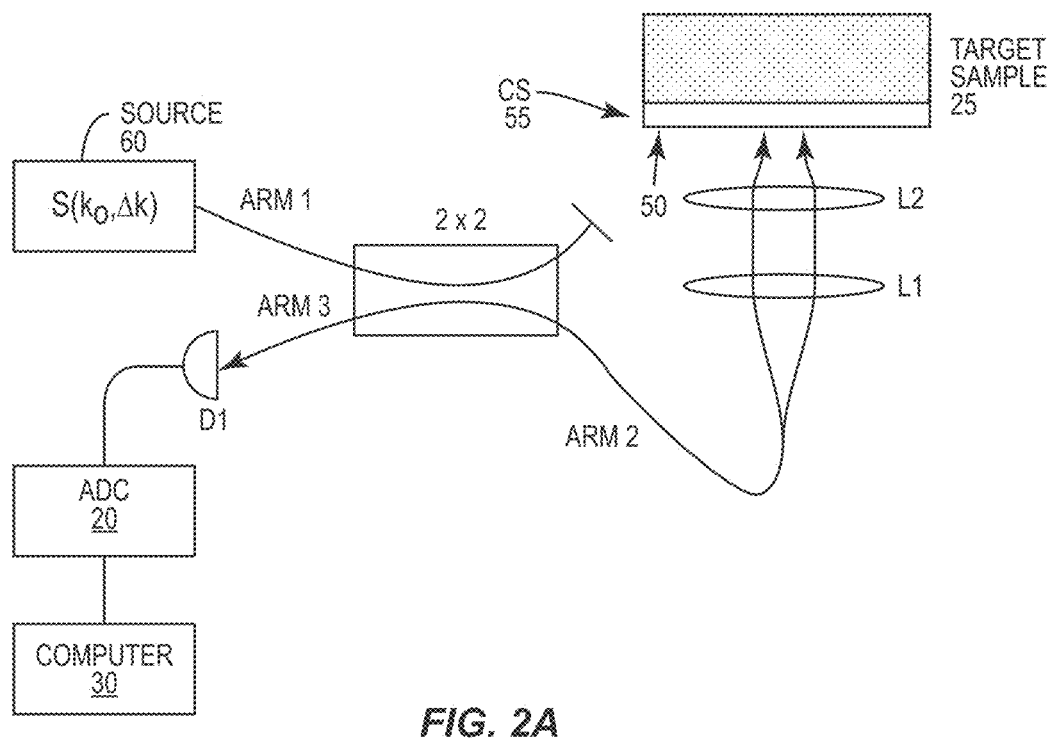
FIG. 2A is a diagram illustrating a spectral-domain-based phase-sensitive OCT.
Figure 2B:
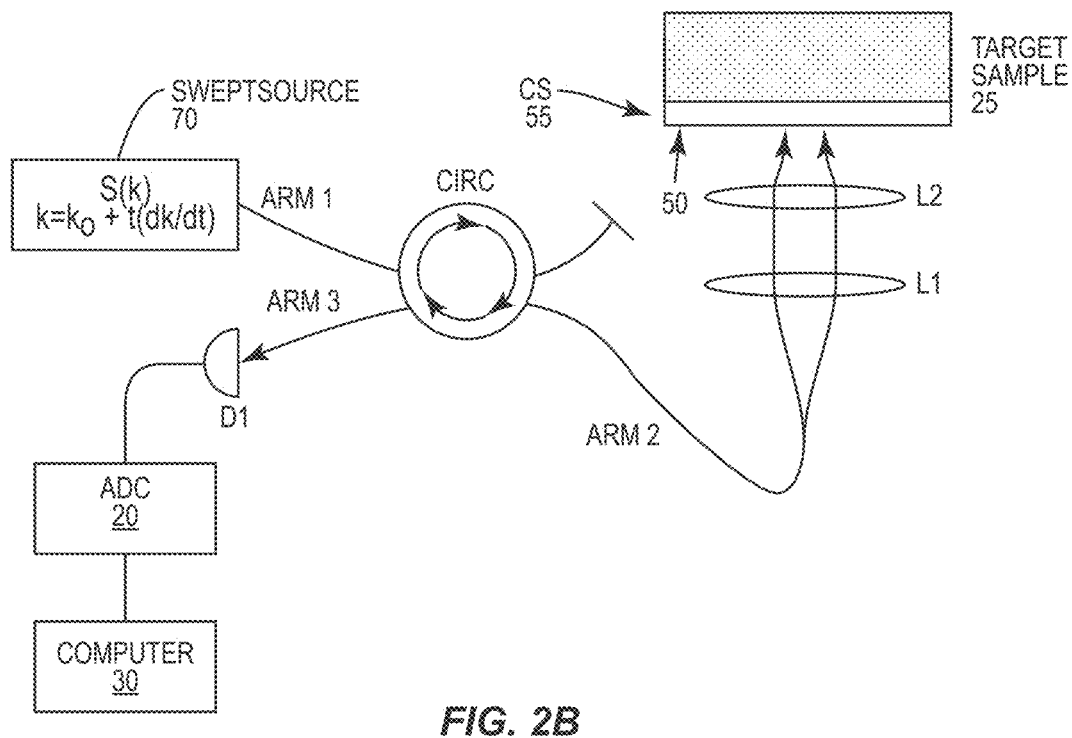
FIG. 2B is a diagram illustrating a spectral-domain-based phase-sensitive OCT.

System 100 further includes the phase-sensitive Optical Coherence Tomographic (OCT) imaging and measurement system 120, which may correspond, in some embodiments, to equipment like that illustrated in FIGS. 1 and 2. The OCT imaging and measurement system 120 can generate an OCT image of the imaged region, as well as phase-sensitive OCT measurements. The OCT imaging and measurement system can be configured to generate an A-scan or a B-scan of the imaged region, using conventional OCT imaging techniques, as well as phase-sensitive phase difference measurements as described. The OCT image and/or measurement information can be outputted in an "OCT out" signal that can be used by analyzer 140.

OCT imaging and measurement system 120 can include an OCT laser operating at a wavelength range of 500-2,000 nm, in some embodiments at a range of 900-1,400 nm. The OCT imaging and measurement system 120 can be based on time-domain, frequency-domain, swept-source, or Fourier Domain Mode Locking (FDML) OCT techniques.

In various embodiments, part of the OCT imaging and measurement system 120 can be integrated into the microscope, and part of it can be installed in a separate console. In some embodiments, the OCT portion integrated into the microscope can include only an OCT light source, such as the OCT laser. The OCT laser or imaging light, returned from the eye, can be fed into a fiber and driven to a second portion of the OCT imaging and measurement system 120, an OCT interferometer outside the microscope. The OCT interferometer can be located in a separate console, in some embodiments, where suitable electronics is also located to process the OCT interferometric signals.

Embodiments of the OCT laser can have a coherence length that is longer than an extent of an anterior chamber of the eye, such as the distance between a corneal apex to a lens apex. This distance is approximately 6 mm in most patients, thus such embodiments can have a coherence length in the 4-10 mm range. Other embodiments can have a coherence length to cover an entire axial length of the eye, such as 30-50 mm. Yet others can have an intermediate coherence length, such as in the 10-30 mm range, finally some embodiments can have a coherence length longer than 50 mm. Some swept-frequency lasers are approaching these coherence length ranges. Some Fourier Domain Mode Locking (FDML) lasers are already capable of delivering a laser beam with a coherence length in these ranges.

In some systems, the OCT imaging and measurement system 120 can be integrated via a microscope interface 150 that can include a beam splitter 152c to provide an optical coupling into the main optical pathway of the microscope 112 or slit-lamp. A mirror 154-2 can couple the light of the OCT 120 into the optical path. The microscope interface 150, its beam splitter 152c, and mirror 154-2 can integrate the OCT imaging and measurement system 120 with the eye-visualization system 110.

FIG. 5 shows that the system 100 can include a second beam splitter 152b, in addition to beam splitter 152c. While beam splitter 152c directs light between the objective 113 and the integrated OCT imaging and measurement system 120, beam splitter 152b can direct light between a display 160 and the binocular 117.

The analyzer, or controller, 140 can perform a variety of integrated biometrical analysis based on the received OCT image and measurement information. In particular, controller 140 may produce a wavefront map of the cornea, in some embodiments, based on the phase-sensitive OCT measurement information provided by OCT imaging and measurement system 120. The analysis can make use of a wide variety of well-known optical software systems and products, including ray tracing software and computer-aided design (CAD) software. The result of the integrated biometry can be (1) a value of the optical power of portions of the eye and a corresponding suggested or prescribed diopter for a suitable IOL; (2) a value and an orientation of an astigmatism of the cornea, and suggested or prescribed toric parameters of a toric IOL to compensate this astigmatism;

and (3) a suggested or prescribed location and length of one or more relaxing incisions to correct this astigmatism, among others.

In intraoperative applications, analyzer 140 can output the result of this integrated biometry towards the display 160, so that the display 160 can display these results for the surgeon. Display 160 can be an electronic video-display or a computerized display, associated with the eye-visualization system 110. In other embodiments, the display 160 can be a display in close proximity of the microscope 112, such as attached to the outside of the microscope 112. Finally, in some embodiments, display 160 can be a micro-display, or heads-up display, that projects the display light into the optical pathway of the microscope 112. The projection can be coupled into the main optical pathway via a mirror 157. In other embodiments, the entire heads-up display 160 can be located inside the microscope 112, or integrated with a port of the microscope 112.

FIG. 5 illustrates such an embodiment, where the display 160 is a heads-up display that projects the biometric information back towards the microscope interface 150 via the mirror 157. In such embodiments, microscope interface 150 contains a beam splitter 152c that redirects the light of the OCT imaging and measurement system 120 towards the patient's eye and redirects the light reflected from the eye 10 towards the OCT imaging and measurement system 120. Beam splitter 152b, as discussed above, redirects the display light from the heads-up display 160 towards the binocular or ocular 117 of the microscope, so that the surgeon can view the displayed biometric information intra-operatively and make informed decisions based on this displayed biometrics.

Figure 6:
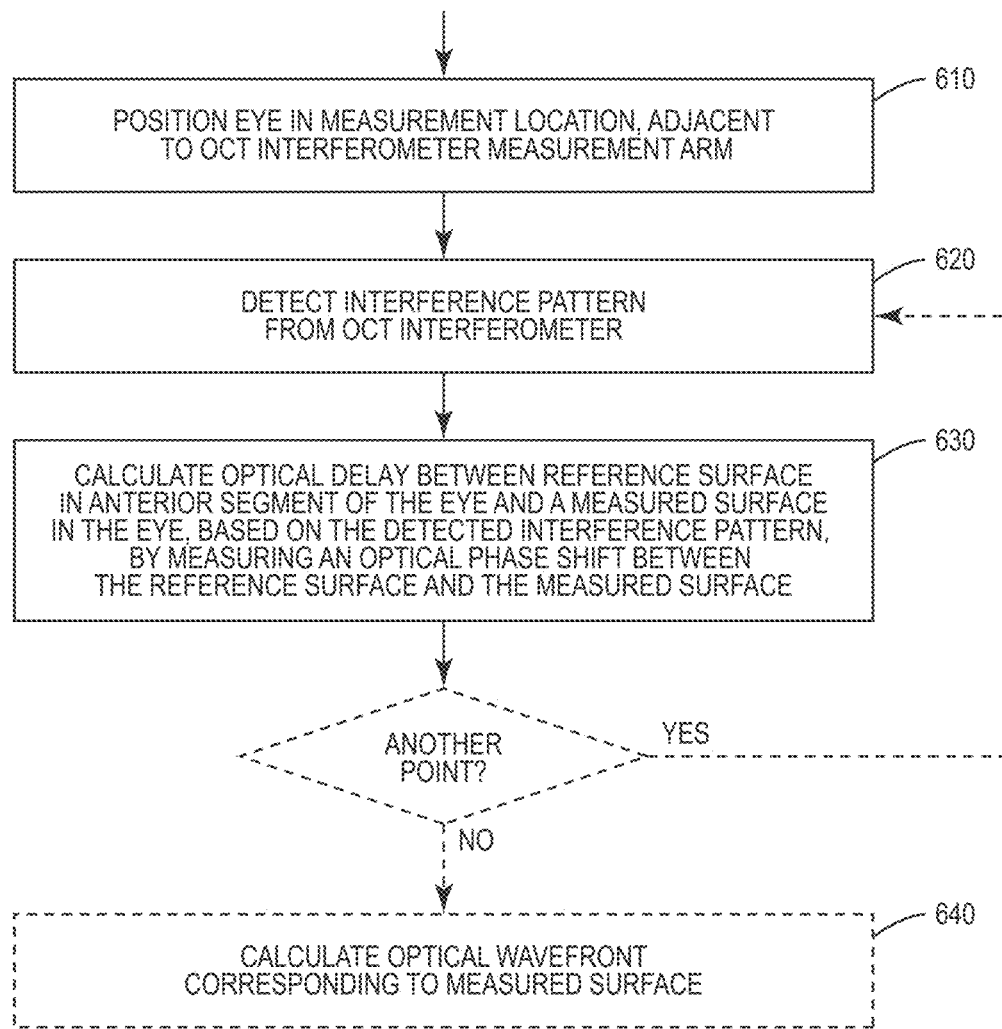
FIG. 6 is a process flow diagram illustrating an example method according to techniques disclosed herein.

FIG. 6 is a process flow diagram illustrating an example method for determining optical aberrations of the anterior segment of an eye, using phase-sensitive OCT measurements. The method of FIG. 6, and variants thereof, may be carried out with an apparatus like that shown in FIG. 5, or in other apparatus configured to carry out phase-sensitive OCT measurements.

As shown at block 610, the method begins with positioning the eye in a measurement location adjacent to a measurement arm of an optical coherence tomography (OCT) interferometer apparatus, so that source light from the measurement arm passes into the anterior segment of the eye. The method continues, as shown at block 620, with detecting an interference pattern from the OCT interferometer apparatus. The interference pattern results from a combination, in the OCT interferometer apparatus, of light reflected from the eye and light reflected from a reference arm of the OCT interferometer apparatus.

As shown at block 630, the method continues with the calculation of an optical delay between a reference surface in the anterior segment of the eye and a measured surface in the eye, based on the detected interference pattern. In some embodiments or instances, the reference surface is the anterior surface of the eye's cornea 12 (see FIG. 5) or the anterior surface of the eye's lens 14 (see FIG. 5) or the anterior surface of the retina 16 (see FIG. 5). The calculating of this optical delay comprises measuring an optical phase shift between the reference surface and the measured surface, based on the detected interference pattern. Techniques for determining this optical phase shift were described above, in the background section. Accordingly, time-domain-based or spectral-domain-based techniques may be used, in various embodiments. However, in the process illustrated in FIG. 6, the reference surface is a surface of the eye itself, rather than the surface of a coverslip introduced between the OCT measurement arm and the target of the measurement. Thus, the process shown in FIG. 6 is performed without any coverslip positioned between the eye and the measurement arm of the interferometer.

In some embodiments, the method shown in FIG. 6 may further comprise scanning the source light in a scan pattern across the measured surface in the eye, such that the detecting and calculating of blocks 620 and 630 repeated for each of a plurality of points in the scan pattern, so as to obtain an optical delay between the reference surface and the measured surface for each of the plurality of points. In some of these embodiments, the the reference surface is the anterior surface of the eye's cornea and the method further comprises calculating an optical wavefront for the cornea, based on the optical delay between the reference surface and the measured surface for each of the plurality of points. This is illustrated at block 640 of FIG. 6. In other embodiments, the reference surface is the anterior surface of the eye's lens and the method further comprises calculating an optical wavefront for the lens, based on the optical delay between the reference surface and the measured surface for each of the plurality of points.

It will be appreciated that the optical delay measurements made using the phase-sensitive OCT techniques described above can be combined with OCT intensity data obtained using conventional OCT processing. This combining of information can be advantageously used, for example, to characterize the uniformity (or lack thereof) of the index of refraction of the eye's lens or cornea, which is information that is not obtainable from conventional OCT intensity data alone. This characterization of the uniformity of the index of refraction might be used, for example, to determine whether a patient is a good candidate for laser-based surgical procedures, where less uniformity of index of refraction of the lens may indicate a lower likelihood of satisfactory results from the surgery.

Thus, in some embodiments, the techniques described herein may further include determining a uniformity of the index of refraction of a component of the eye, based on the optical delay between the reference surface and the measured surface for each of the plurality of points and further based on OCT intensity data for the reference surface or the measured surface, or both.

The specific embodiments described above illustrate but do not limit the invention. It should also be understood that numerous modifications and variations are possible in accordance with the principles of the present invention, as described above and as claimed below.

What is claimed is:

1. A method for determining optical aberrations of the anterior segment of an eye, the method comprising:
   positioning the eye in a measurement location adjacent to a measurement arm of an optical coherence tomography (OCT) interferometer apparatus, so that source light from the measurement arm passes into the anterior segment of the eye;
   detecting an interference pattern from the OCT interferometer apparatus, the interference pattern resulting from a combination, in the OCT interferometer apparatus, of light reflected from the eye and light reflected from a reference arm of the OCT interferometer apparatus; and
   based on the detected interference pattern, calculating an optical delay between a reference surface in the anterior segment of the eye and a measured surface in the eye, the reference surface being the anterior surface of the eye's cornea or the anterior surface of the eye's lens, wherein said calculating comprises measuring an optical phase shift between the reference surface and the measured surface, based on the detected interference pattern.

2. The method of claim 1, wherein the method further comprises scanning the source light in a scan pattern across the measured surface in the eye, and wherein said detecting and calculating are repeated for each of a plurality of points in the scan pattern, so as to obtain an optical delay between the reference surface and the measured surface for each of the plurality of points.

3. The method of claim 2, wherein the reference surface is the anterior surface of the eye's cornea and the method further comprises calculating an optical wavefront for the cornea, based on the distance between the reference surface and the measured surface for each of the plurality of points.

4. The method of claim 2, wherein the reference surface is the anterior surface of the eye's lens and the method further comprises calculating an optical wavefront for the lens, based on the distance between the reference surface and the measured surface for each of the plurality of points.

5. The method of claim 2, wherein the method further comprises determining a uniformity of the index of refraction of a component of the eye, based on the optical delay between the reference surface and the measured surface for each of the plurality of points and further based on OCT intensity data for the reference surface or the measured surface, or both.

6. The method of claim 1, wherein the method is performed without a coverslip positioned between the eye and the measurement arm of the interferometer.

7. The method of claim 1, wherein said detecting is performed using time-domain OCT.

8. The method of claim 1, wherein said detecting is performed using spectral-domain OCT.

* * * * *